United States Patent [19]
Harris et al.

[11] Patent Number: 4,938,206
[45] Date of Patent: Jul. 3, 1990

[54] FLOATING PIVOT HINGE AND KNEE BRACE

[75] Inventors: David P. Harris; Michael E. Berkeley, both of Aspen; William L. McCune, Denver, all of Colo.

[73] Assignee: Design Medical, Inc., Aspen, Colo.

[21] Appl. No.: 8,196

[22] Filed: Jan. 29, 1987

Related U.S. Application Data

[63] Continuation-in-part of Ser. No. 943,554, Dec. 18, 1986, abandoned.

[51] Int. Cl.$^5$ .............................................. A61F 5/04
[52] U.S. Cl. .................................. 128/80 F; 128/80 C
[58] Field of Search ...................... 128/80 C, 80 F, 98

[56] References Cited

U.S. PATENT DOCUMENTS

| | | | |
|---|---|---|---|
| 1,390,915 | 9/1921 | Loth | 623/39 |
| 2,382,679 | 8/1945 | Tollman | 128/80 F |
| 2,485,036 | 10/1949 | Christopher | 128/80 F |
| 2,516,872 | 8/1950 | Houser et al. | 128/80 H |
| 2,632,440 | 3/1953 | House et al. | 128/80 F |
| 2,910,310 | 10/1959 | Mulac | 285/91 |
| 3,779,654 | 12/1973 | Horne | 128/80 C |
| 3,826,251 | 7/1974 | Ross | 128/80 F |
| 4,136,404 | 1/1979 | Lange | 128/80 R |
| 4,353,361 | 10/1982 | Foster | 120/80 C |
| 4,361,142 | 11/1982 | Lewis et al. | 128/80 C |
| 4,372,298 | 2/1983 | Lerman | 128/80 C |
| 4,392,488 | 7/1983 | Will | 128/80 F |
| 4,409,689 | 10/1983 | Buring et al. | 128/80 C |
| 4,433,679 | 2/1984 | Mauldin et al. | 128/80 F |
| 4,463,751 | 7/1984 | Bledsoe | 128/80 C |
| 4,531,731 | 7/1985 | Low | 128/80 C |
| 4,617,920 | 10/1986 | Carsalade | 128/80 C |
| 4,620,532 | 11/1986 | Houseworth | 128/80 C |
| 4,637,382 | 1/1987 | Walker . | |
| 4,688,559 | 8/1987 | Vito et al. | 128/80 F |
| 4,691,697 | 9/1987 | Arensdorf et al. | 128/80 C |
| 4,697,583 | 10/1987 | Mason et al. | 128/80 C |

FOREIGN PATENT DOCUMENTS

| | | |
|---|---|---|
| 424467 | 12/1924 | Fed. Rep. of Germany . |
| 473487 | 2/1929 | Fed. Rep. of Germany . |

OTHER PUBLICATIONS

W. Muller, "The Knee," Springer-Verlag, Berlin, Heidelberg, New York 1983, pp.8-13.
V. Frankel, "Basic Biomechanics of the Skeletal System," Lea & Febiger, Philadelphia 1980, pp. 113-125.

*Primary Examiner*—Edgar S. Burr
*Assistant Examiner*—Tonya Lamb
*Attorney, Agent, or Firm*—Ralph F. Crandell; Holland & Hart

[57] ABSTRACT

A knee brace includes a thigh cuff having inner and outer spaced brace arms adapted to extend along the user's thigh toward the knee, a calf cuff including inner and outer spaced brace arms adapted to extend along the user's calf toward the knee, and floating pivot axis hinges rotatably connecting the inner and outer brace arms of each pair. The hinge is formed by a pair of juxtaposed hinge plates, each having a pivot face in opposition to a pivot face on the juxtaposed plate, with a concave groove in each of the face. A pivot bearing ball is confined between the opposed faces and retained in the concave grooves. A spring, bellville spring, or disk spring biases the hinge plates together when the pivot bearing ball is positioned in the opposed grooves between. The pivot bearing ball provides a floating pivot axis for hinge rotation of said hinge plates and thereby said braces relative to each other, the ball and concave grooves allowing the hinge plates simultaneously to slide and pivot relative to each other. The pivot axis floats between the hinge plates depending on the degree of pivoting and sliding movement in a wearer's knee joint as a result of flexion thereof.

16 Claims, 5 Drawing Sheets

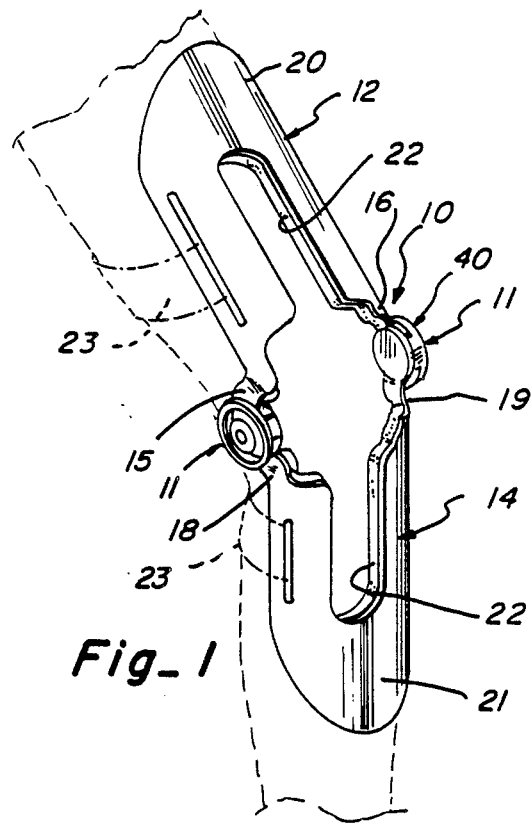
Fig_1
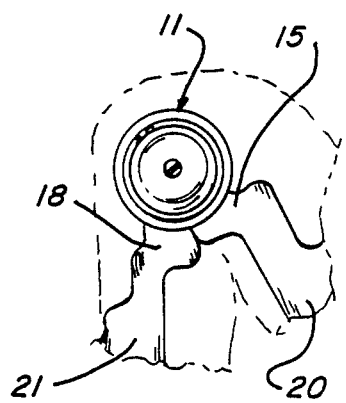
Fig_4
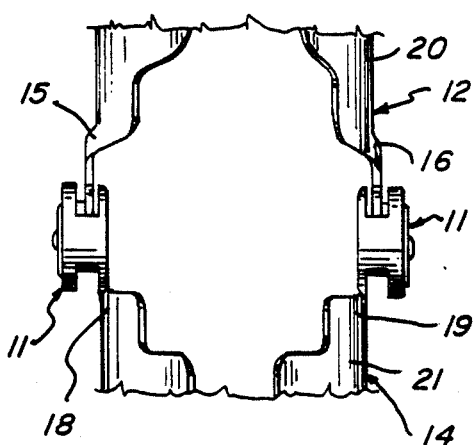
Fig_2
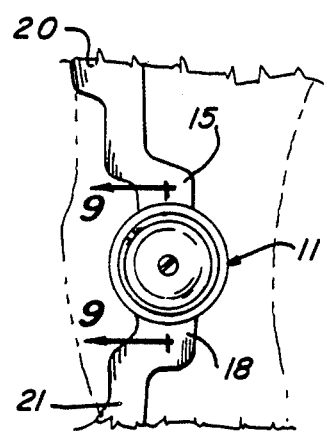
Fig_3

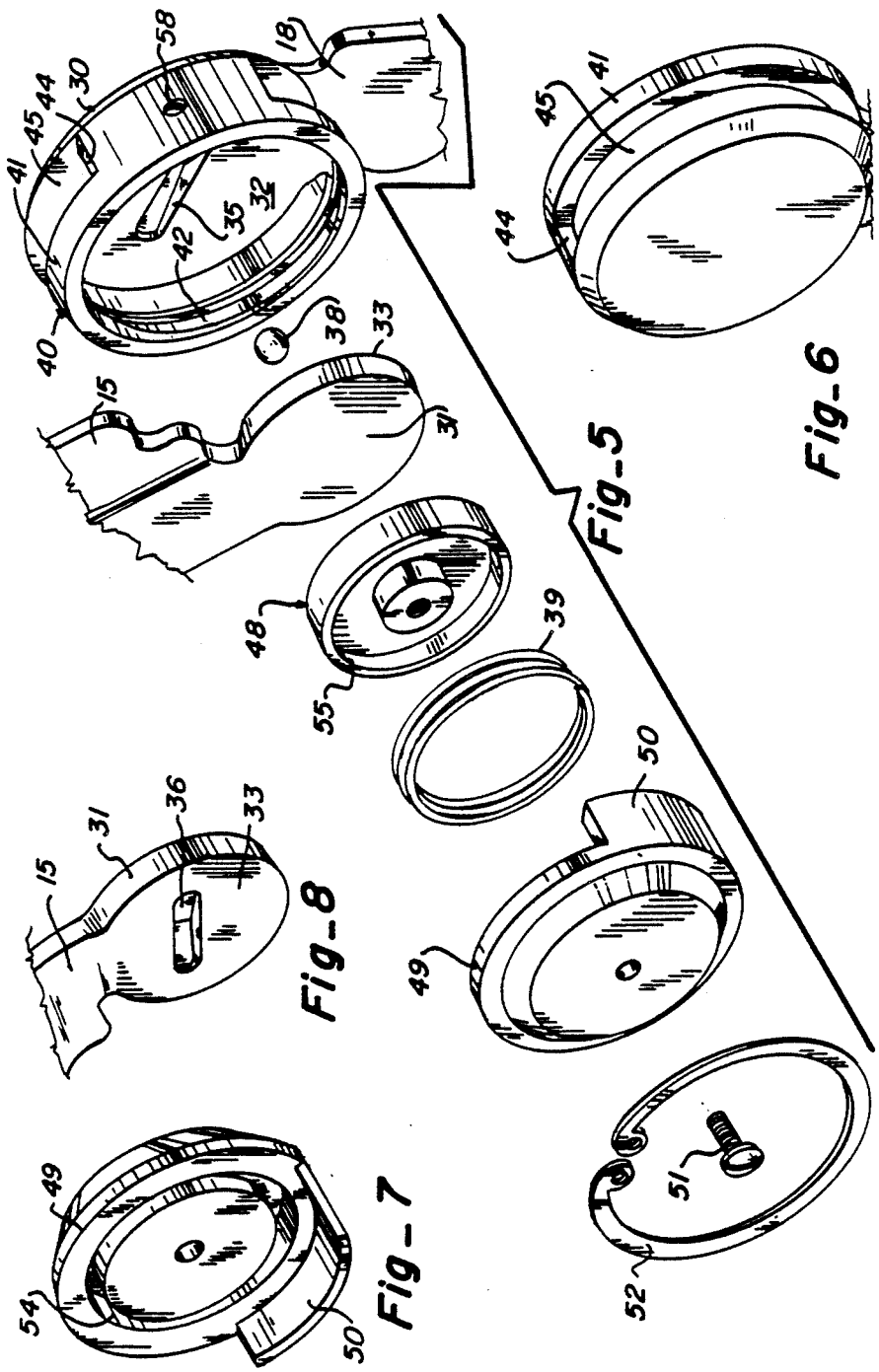

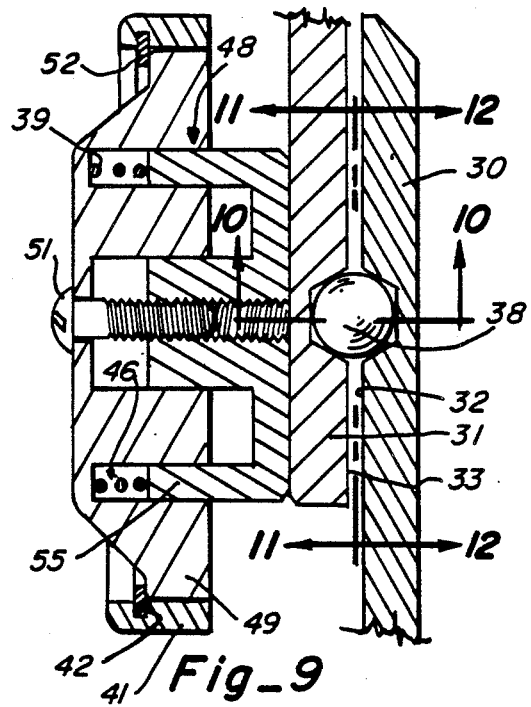
Fig_9
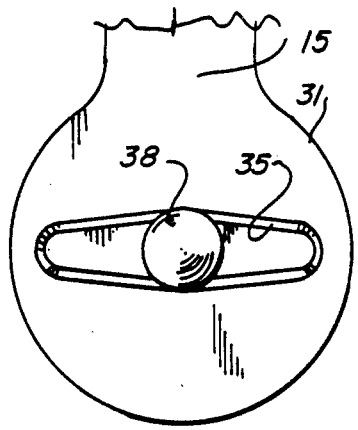
Fig_11
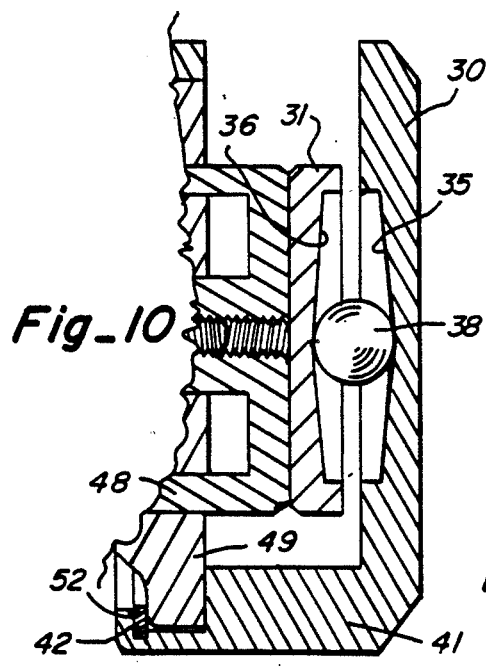
Fig_10
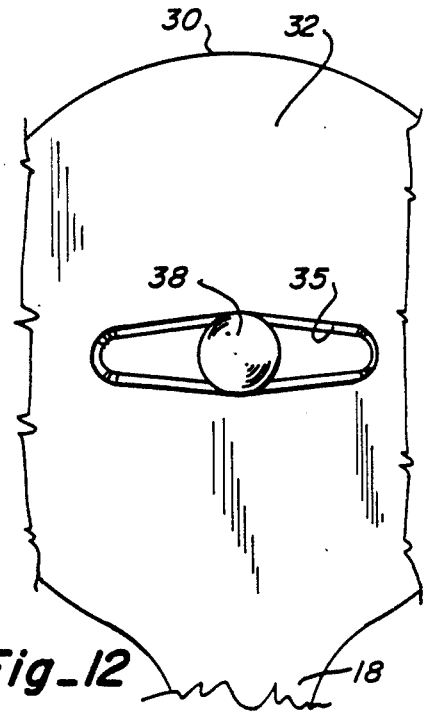
Fig_12

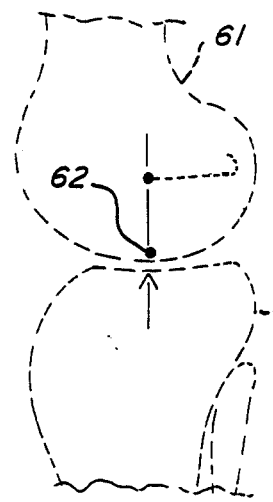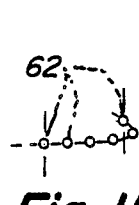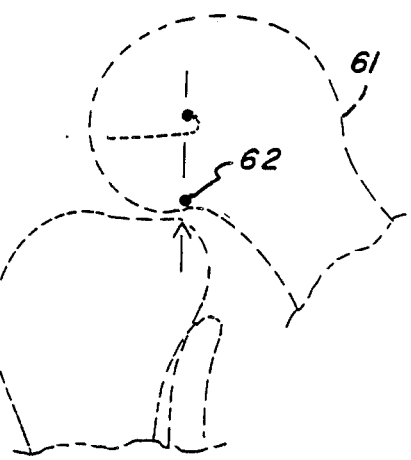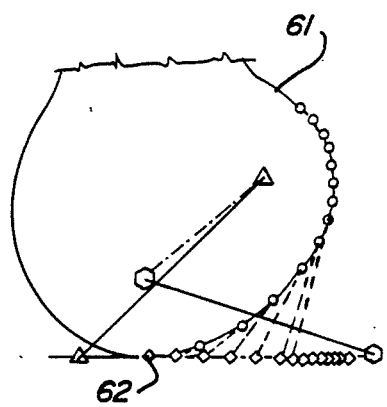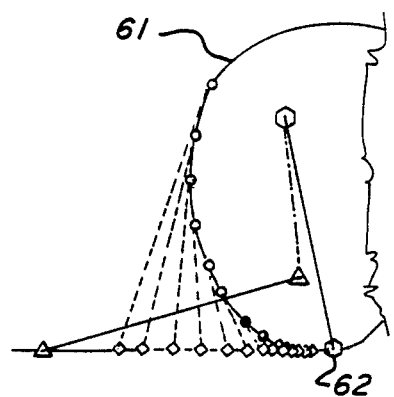
Fig_13  Fig_15  Fig_14  Fig_16  Fig_17

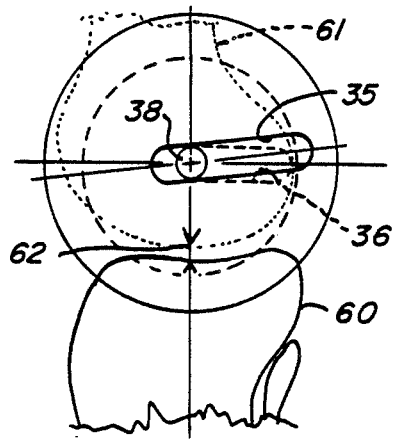
Fig_18
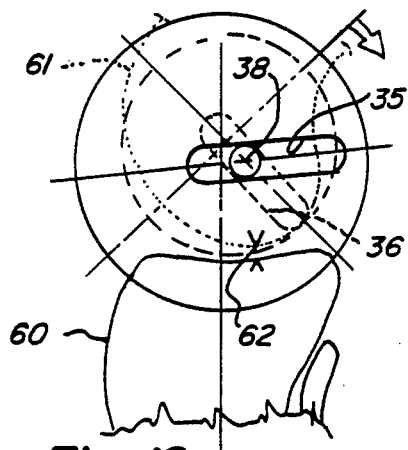
Fig_19
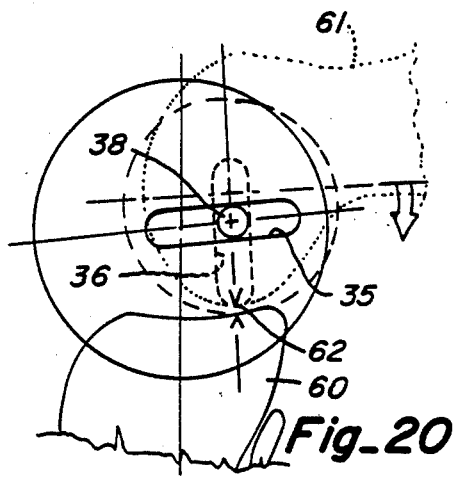
Fig_20
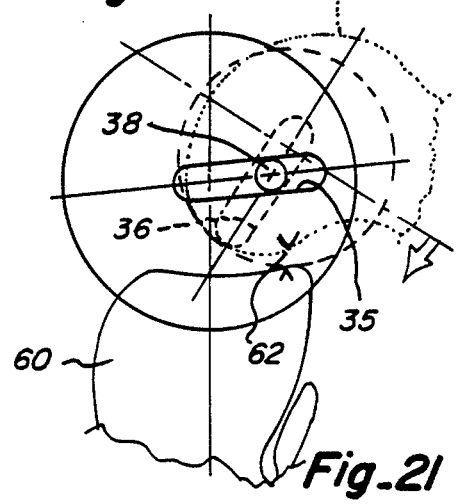
Fig_21
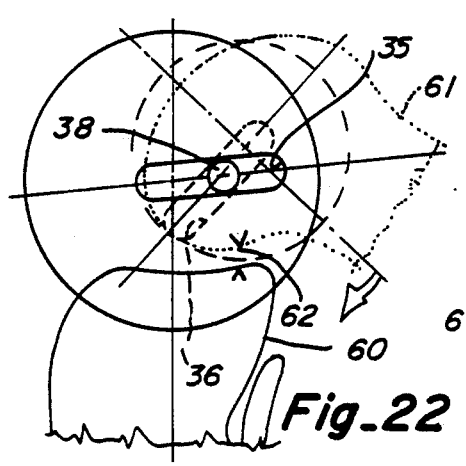
Fig_22
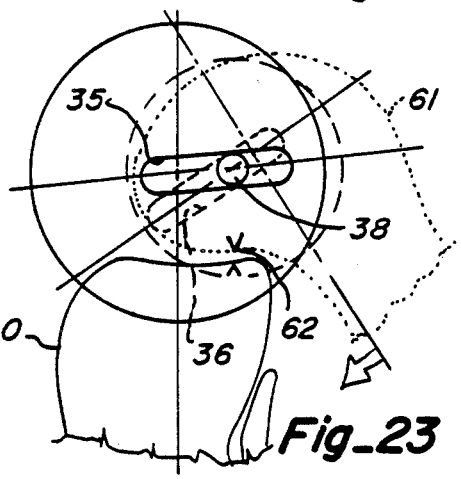
Fig_23

FLOATING PIVOT HINGE AND KNEE BRACE

CROSS-REFERENCE TO RELATED APPLICATION

This application is a continuation-in-part of co-pending application Ser. No. 06/943,554 filed December 18, 1986 for FLOATING PIVOT HINGE AND KNEE BRACE, now abandoned.

BACKGROUND OF THE INVENTION

1. Field of the Invention

The present invention relates to a hinge, and more particularly to a hinge with a floating pivot point or axis. Hinges of the type herein described find particular but not necessarily exclusive utility in orthopedic supports and more particularly in knee braces. More specifically, the present invention relates to a hinged knee brace for restraining a knee while permitting normal movement thereof, such as by restraining rotation and dislocation or subluxation of a tibia with respect to a femur in a wearer's leg.

2. Description of the Prior Art

Extensive studies have shown that the human knee joint is a complex mechanism, and that the knee does not provide a single axis of rotation between the femur (thigh bone) and tibia (leg bone). During flexing and extension of the leg, the axis of rotation between the femur and tibia moves laterally, defining a generally J-shaped path. This results from both a rotating and a sliding movement in the knee joint.

Any attempt to provide a knee brace that limits the movement of the limbs about a single axis not only causes discomfort to the wearer, but can cause damage to the knee joint. Where such a single-pivot axis brace is secured to both the thigh and the calf, a sliding movement along the leg is created, abrading the skin and causing substantial discomfort, as well as limiting effective leg movement.

Referring, for example, to U.S. Pat. No. 3,669,105, issued June 13, 1972, to I. F. Castigla for "Brace for Articulated Limbs," and a similar brace with an adjustable hinge as shown in U.S. Pat. No. 3,785,372, issued January 15, 1974, to W. A. Craig for "Extension Desubluxation Hinge Appliance," the single pivot axis shown causes the supporting pads to slide on the leg as the knee is flexed. To relieve such sliding movement, the pads are necessarily soft and flexible, thereby reducing the effectiveness of the brace.

A variety of devices have been developed in an effort to provide the complex pivoting movement associated with the knee joint, while at the same time providing the necessary support for the knee and leg. See, for example, U.S. Pat. No. 4,489,718, and published U.K. Pat. Appl'n No. GB2139896A. These various devices are complex and accordingly are necessarily heavy and cumbersome. In most instances, the devices severely limit the natural sliding and pivoting movement of the knee. Knee braces with double pivot point or polycentric hinges are shown in U.S. Pat. No. 4,271,831 and published European Patent Specification No. 0070411.

A number of prior art patents disclose multicentric hinges for leg and knee braces. See U.S. Pat. No. 4,320,747; U.S. Pat. No. 4,463,751; U.S. Pat. No. 4,379,463; U.S. Pat. No. 3,817,244; and U.S. Pat. No. 4,409,689.

OBJECTS OF THE INVENTION

It is the principal object of the present invention to provide an improved knee brace which allows normal flexing movement of the leg at the knee joint, that is flexing movement between the tibia and the femur, while restraining abnormal twisting of the tibia with respect to the femur, medically referred to as a varus movement, and restraining horizontal or sidewise movement of the tibia with respect to the femur, commonly referred to as a bow leg or knock-kneed position and medically referred to as a valgus movement.

It is a related object of the present invention to provide a knee brace including a hinge that tracks or recognizes both the pivoting and the sliding movements of the knee joint as the leg is straightened or extended and flexed.

A further object of the present invention is to provide a knee brace of the foregoing character which provides for limited movement of the wearer's leg between a relatively straight position and a flexed position, and restricts flexing and extending of the knee beyond predetermined limits.

Still another object of the present invention is to provide a knee brace of the foregoing character wherein valgus and varus movements of the tibia with respect to the femur are restricted.

Still another object of the present invention is to provide a knee brace of the foregoing character in which the hinge is a modular component adapted for use in both surgical postoperative braces and athletic braces.

Still another object of the present invention is to provide a knee brace of the foregoing character wherein the hinge mechanism is adjustable to provide both an adjustable and variable resistance to movement of the floating pivot axis therein.

Still another object of the present invention is to provide a knee brace of the foregoing character in which the hinge pivot axis floats or shifts from a central basic point in accordance with the sliding and pivoting movement of the human knee, and with the resistance to shifting of the pivot axis increasing as the pivot axis moves away from the optimum or basic pivot point.

A related object is to provide an improved hinge with a floating pivot axis, and particularly a floating pivot point or axis that tracks the movement of a knee or similar joint.

Other objects and advantages of the present invention will become apparent from the following description taken in connection with the accompanying drawings.

SUMMARY OF THE INVENTION

A knee brace incorporating a floating pivot point or pivot axis hinge includes conventional leg cuffs, each with a pair of brace members or brace arms. Each pair of braces is adapted to be positioned alongside a wearer's leg, and extends towards the knee. A hinge secures together the braces on one side of the leg and knee, connecting respectively a thigh brace arm with the corresponding calf brace arm. The present invention is particularly concerned with the construction of the hinges, which incorporate a floating pivot point or axis in order to accommodate the natural sliding and pivoting movements of the human knee joint.

The cuffs may be of any appropriate configuration and construction, the comfort of the wearer being the primary concern. Each cuff includes a pair of spaced-apart brace members or arms extending from a concave or curved cylindrical channel-shaped cuff support adapted to engage partially around a wearer's leg. Straps and velcro or similar fasteners are secured to the cuffs and adapted to extend around the wearer's leg to hold the cuff support thereon. Various forms of padding may be utilized under the cuff supports and on the condyle facing areas of the hinges.

The hinge construction embodying the present invention comprises a pair of opposed hinge plates, one of which is secured to a calf brace arm and the other of which is secured to the corresponding thigh brace arm. The hinge plate may be formed as an integral part of the brace arm to which it is attached or may be formed separately and bolted, riveted or otherwise secured to the respective arm or brace. Each hinge plate is provided on its face surface; that is, the surface which opposes a similar face surface on the opposed plate, with a horizontally extending concave groove. The groove in the face of each plate extends generally perpendicular or normal to the longitudinal axis of the arm or brace associated with or fixed to the hinge plate.

A pivot axis extending between the two hinge plates normal to the hinge plate face surfaces is provided by a ball bearing positioned and riding in the respective opposed grooves for rolling, sliding and pivoting movement therein. The location of the bearing pivot ball in the respective grooves provides a single floating pivot axis between the two hinge plates. With such a ball pivot, the plates may slide relative to each other within the limits defined by the grooves, and may rotate or pivot with respect to each other about the pivot axis formed by the ball bearing. The pivot axis extends diametrically through the pivot ball and normal to the face surfaces of the hinge plates.

The hinge plates are biased towards each other by a coil, disc, finger or bellville spring or like spring biasing member mounted on one or both sides of the hinge plates. The spring acts to urge the hinge plates together on the enclosed pivot ball. The ball is retained in the grooves by the force of the spring thereon.

The hinge plates and enclosed pivot bearing ball and biasing spring are housed within an appropriate housing. A housing ring or sleeve cap having an internal snap ring groove defined therein includes an annular segmental lip securing said ring in spaced relation to a hinge plate. The housing ring may be formed as an integral part of the plate or may be secured thereto. The space between the ring and the face of the hinge plate defines an annular slot through which the second hinge plate and brace arm extends. When the hinge plates are in juxtaposed relation, the face surfaces and confined pivot bearing ball are retained by the action of a spring assembly. As the plates slide relative to each other the force on the bearing pivot is increased as the depth of the grooves decreases thereby compressing the biasing spring. The ball pivot is normally at the center of the concave depression in each plate, being generally the "at rest" position of the hinge. In this position the hinge plates can rotate relative to each other with an minimum of force on the ball. As the plates slide relative to each other, the pivot axis of the ball shifts while the plates retain their ability to pivot about the ball axis.

DESCRIPTION OF THE DRAWINGS

FIG. 1 is an isometric view of a knee brace and floating pivot axis hinge embodying the present invention.

FIG. 2 is an enlarged, partial, front elevation view of the knee brace and hinge structure shown in FIG. 1.

FIG. 3 is an enlarged, partial, side elevation view of the knee brace and hinge shown in FIG. 1 with the leg and knee in a straight or extended position.

FIG. 4 is an enlarged, partial, side elevation view of the knee brace and hinge shown in FIG. 1 with the leg and knee in a flexed position.

FIG. 5 is an englarged, isometric, exploded view of the hinge structure shown in FIG. 1.

FIG. 6 is an enlarged, isometric view of the outer cage and bearing plate portion of the hinge shown in FIG. 5 but taken from the side opposite to the side thereof shown in FIG. 5.

FIG. 7 is an enlarged, isometric view of the inner cap portion of the hinge shown in FIG. 5, but taken from the side opposite the side thereof shown in FIG. 5.

FIG. 8 is an enlarged, isometric view of the inner bearing plate portion of the hinge shown in FIG. 5, but taken from the side opposite to the side thereof shown in FIG. 5.

FIG. 9 is an enlarged vertical cross section view through the hinge taken substantially in the plane of line 9—9 on FIG. 3.

FIG. 10 is a section view taken substantially in the plane of line 10—10 on FIG. 9.

FIG. 11 is a section view taken substantially in the plane of line 11—11 on FIG. 9.

FIG. 12 is a section view taken substantially in the plane of line 12—12 on FIG. 9.

FIG. 13 is a diagramatic representation of a knee joint including the upper thigh bone or femur, the lower leg bone or tibia and showing the contact point between the two with the femur and tibia aligned generally in a straight line.

FIG. 14 is a diagramatic view similar to FIG. 13 but showing a knee joint substantially flexed.

FIG. 15 is a diagramatic representation of a "J" curve illustrating the combination of pivoting and sliding movement encountered in a knee joint.

FIGS. 16 and 17 are diagramatic representations of the locus of points of contact in a knee joint between the femur and the tibia during flexion or extension of the leg.

FIG. 18 is a diagramatic representation of a knee joint and a hinge embodying the present invention, with the knee joint substantially in the position shown in FIG. 13.

FIG. 19 is a view similar to FIG. 18 but illustrating the knee partially flexed.

FIG. 20 is a diagramatic representation similar to FIG. 18, but with the knee joint flexed to approximately a 90° angle.

FIG. 21 is a diagramatic representation similar to FIG. 18, but with the knee joint still further flexed.

FIG. 22 is a diagramatic view similar to FIG. 18 but showing the knee joint still further flexed.

FIG. 23 is a diagramatic view similar to FIG. 18 but illustrating the knee joint substantially flexed and with the tibia at approximately a 30° angle with respect to the femur.

DESCRIPTION OF THE PREFERRED EMBODIMENT

A knee brace 10 incorporating a floating pivot point or pivot axis hinge 11 embodying the present invention includes a conventional thigh cuff 12 and calf cuff 14, each with a pair of brace members or brace arms 15, 16, and 18, 19, respectively, which members or arms are usually referred to herein as braces. Each pair of braces is adapted to be positioned alongside a wearer's leg, and extends towards the knee. A hinge 11 secures together the braces on one side of the leg and knee, connecting respectively a thigh brace arm 15, 16 with the corresponding calf brace arm 18, 19. The present invention is particularly concerned with the construction of the hinges 11, which provide a floating pivot point or axis to the hinge in order to accommodate the natural sliding and pivoting movements of the human knee joint as illustrated in FIGS. 13–17.

The thigh cuff 12 and calf cuff 14 may be of any appropriate configuration and construction, the comfort of the wearer being the primary concern. In the form shown in FIGS. 1 and 2, each cuff 12, 14 includes a pair of spaced-apart brace members or arms 15, 16, and 18, 19, respectively, extending from a concave or curved cylindrical channel-shaped cuff support 20, 21 adapted to engage partially around a wearer's leg. Straps 23 and velcro or similar fasteners are secured to the cuff supports 20, 21 and adapted to extend around the wearer's leg to hold the cuff support thereon. Various forms of padding 22 may be utilized under the cuff supports 20, 21 and on the condyle facing areas of the hinges.

The hinge construction embodying the present invention comprises a pair of opposed hinge plates 30, 31, one of which 30 is secured to a calf brace arm 18, 19 and the other of which is secured to the corresponding thigh brace arm 12, 14. If desired, the hinge plates 30, 31 may be formed as an integral part of the brace arm to which it is attached or may be formed separately and bolted, riveted or otherwise secured to the respective arm or brace. Each hinge plate 30, 31 is provided on its face surface 32, 33, respectively, that is the surface which opposes a similar face surface on the opposed plate, with a horizontally extending concave groove 35, 36, respectively. The groove 35, 36 in the face 32, 33 of each plate 30, 31 extends, in the preferred embodiment, diametrically of the hinge plate and generally perpendicular or normal to the longitudinal axis of the arm or brace associated with or fixed to the plate, to which the hinge plate 30, 31 is secured.

A pivot axis extending between the two hinge plates normal to the hinge plate face surfaces 32, 33 is provided by a ball bearing 38 positioned and riding in the respective opposed grooves 35, 36 for rolling, sliding and pivoting movement therein. The location of the bearing pivot ball 38 in the respective grooves 35, 36 provides a single floating pivot axis between the two hinge plates 30, 31. With such a ball pivot, the plates 30, 31 may slide relative to each other within the limits defined by the grooves 35, 36, and may rotate or pivot with respect to each other about the pivot axis formed by the ball bearing 38. The pivot axis extends diametrically through the pivot ball 38 and normal to the face surfaces 32, 33 of the hinge plates.

The hinge plates are biased towards each other by a coil, disc, finger or bellville spring 39 or like spring biasing member mounted on one or both sides of the hinge plates 30, 31. The spring 39 acts to urge the hinge plates 30, 31 together on the enclosed pivot ball 38. The ball is retained in the grooves by the force of the spring thereon.

The hinge plates 30, 31 and enclosed pivot bearing ball 38 and biasing spring 39 are housed within an appropriate housing 40. Referring to FIGS. 5–8, an illustrative housing structure comprises a housing ring or sleeve cap 41 having an internal snap ring groove 42 defined therein and having an annular segmental lip 44 securing said ring 41 in spaced relation to a hinge plate 30. The housing ring 41 may be formed as an integral part of the plate 30 or may be secured thereto in any suitable manner. The space between the ring 41 and the face 32 of the hinge plate 30 defines an annular slot 45 through which the second hinge plate 31 and brace arm 15 extends. When the hinge plates 30, 31 are in juxtaposed relation, the face surfaces 32, 33 and confined pivot bearing ball 38 are retained by the action of a spring assembly 46.

The spring assembly includes a biasing spring 39 acting against a housing disc or follower plate 48 and enclosed by a cap 49. The cap 49 further includes an annular segmental shoulder 50 adapted to be inserted into the ring 41 to limit the extent of the annular slot 45. In this manner the segmental lip 50 serves to limit the swinging movement of the upper brace arm 13 with respect to the lower brace arm 18.

The cap 49 and spring follower plate 48 enclose the spring and are secured together by an appropriate threaded fastener 51. The spring assembly 46 is mounted in place in the ring 41 by means of a snap ring 52 which is engaged in the inner annular slot 42 of the ring 41.

Where a coil spring is utilized, the cap 49 includes on its inner face an annular groove 54 for receiving the coils of the coil spring 39. The spring plate 48 includes an annular rim 55 which is telescoping or slidingly received in the slot 54 in the cap and confines the spring 39 within the slot 54. An alternative construction can utilize finger or bellville springs and the cap and spring follower 48 are modified accordingly.

To adjust the length of the slot 45 and thereby the swinging movement of the first brace arm 15 relative to the second brace arm 18, appropriate adjustable stops or set screws 58 are provided. The circumferential length of the slot 45 determines the movement of the respective mounting arms relative to each other and thereby serves to limit the rotational movement of the hinge plates relative to each other about the pivot bearing.

A variety of alternative hinge housing structures may be utilized with each providing means for pressing the hinge plates together over the intermediate ball bearing retained in the hinge plate concave grooves.

Condyle pads may be provided on the inner surface of the hinge structure to prevent the hinge from rubbing against the sides of the knee joint. For some applications it is desirable that the hinge plate fixed to the thigh cuff be the inner plate; that is, the plate closest to the knee and condyle bones thereof. For other applications the hinge plate fixed to the calf cuff may be the inner plate. In both instances, the condyle pads may be placed between the hinge and the knee to support the knee without rubbing the wearer's skin as the knee is flexed and extended.

The structure of the ball pivot and bearing plates is shown in more detail in FIGS. 9–12. Note in FIGS. 11 and 12 the tapered or concave groove adapted to receive the ball bearing pivot. As the plates 30, 31 slide relative to each other the force on the bearing pivot is increased as the depth of the grooves decreases thereby compressing the biasing spring. In the structure shown in FIGS. 11 and 12, the ball is at the center of the concave depression in each plate, being generally the "at rest" position of the hinge. In this position the hinge plates can rotate relative to each other with an minimal of force on the ball. As the plates slide relative to each other, the pivot axis of the ball shifts while the plates retain their ability to pivot about the ball axis.

The pivoting and sliding movement of a knee joint is illustrated diagramatically in FIGS. 13-17. The bones of the knee do not pivot about a single axis but rather involve a complex pivoting and sliding movement. The tibia 60 and femur 61 rotate with respect to each other initially about a pivot or contact point 62. As the knee is flexed this point moves along the surface between the bones while the bones both pivot and slide with respect to each other as shown in FIGS. 14, 16 and 17. A pivot point on the femur, for example, follows a generally "J" shaped curve path. This rotation point is the imaginary point of rotation of the femur with respect to the tibia at any instant in time. Note the path or locus of pivot points of the femur shown in FIGS. 16 and 17 as the tibia and femur flex with respect to each other. This movement requires that the tibia and femur both pivot and slide with respect to each other as demonstrated in FIGS. 16 and 17.

The relationship of the knee brace to a wearer's knee during flexing movement thereof is shown in FIGS. 18 through 23 inclusive. In these figures, the position of the upper or thigh hinge plate and concave groove with respect to the femur is shown in dotted lines, while the position of the lower or calf hinge plate with respect to the tibia is shown in solid lines. For clarity in illustration, the concave grooves are shown in half length. Thus, the ball pivot shown in FIG. 18 is at the deepest point of the grooves, when the leg is relatively straight. For some applications, the groove may deliberately be cut in such a "half" or partial length configuration, particularly where hyperflexion of the knee is to be prevented.

These figures further do not illustrate limitations on flexing movement of the calf brace with respect to the thigh brace and thus limitations on the rotation or pivoting movement of the tibia with respect to the femur are not shown. FIG. 18 illustrates the tibia and femur in generally a vertically aligned position, which would be the normal position for one standing erect or with the leg straightened. In this position, the pivot is generally at the center or deepest point of each groove. Being located at the deepest point of the grooves, the pivot bearing ball is under minimum compression as a result of the action of the biasing spring urging the hinge plates together.

FIG. 19 illustrates a partial flexing movement of the femur with respect to the tibia, providing an included angle of approximately 135° and with the pivot point having moved slightly posteriorly in conjunction with the movement of the pivot point between the tibia and the femur.

FIG. 20 illustrates the knee at approximately a 90° position again with the pivot point of the brace having moved further posteriorly as the knee is flexed. The pivot ball at this point is under increased compression, and the hinge plates have moved posteriorly to accomodate the sliding movement of the knee joint.

FIG. 21 illustrates the knee at approximately a 60° angle, the pivot point having moved further posteriorly, to approximately its outermost position, and the pivot point of the brace having moved similarly.

FIGS. 22 and 23 show further movement and flexing of the knee from a 45° to a 30° position, with the pivot point of the brace floating accordingly and defining a generally J-shaped curve as illustrated in FIG. 15.

The present invention provides a floating pivot point or axis in the knee brace hinge in which the pivot point is urged to seek a "rest" position when the wearer's leg is generally straight and the knee is flexed at a minimum. As the wearer's leg is flexed by bending the knee, the pivot axis of the brace hinge shifts posteriorly. However, during this posterior shift, the pivot axis moves against some resistance tending to return the hinge to the rest position. Similarly, as the wearer's leg is further flexed by flexing the knee joint, the hinge pivot axis shifts against the resistance tending to urge the hinge to its rest position. The degree of resistance is determined primarily by the degree of curvature of the concave groove and the force of the spring tending to hold the hinge plates together. The friction relationship between the ball bearing and the groove also plays a part and can be varied by appropriate friction reducing coatings on the hinge plates and ball pivot, as well as by appropriate lubrication.

By limiting the swinging movement of the brace arms with respect to each other, hyperflexion and hyperextension of the knee can be prevented while allowing normal flexion and extension within predetermined ranges.

The hinge may also be utilized in other supports such as in articulated ski boots wherein the ankle support is hinged to the shoe portion of the boot. Such a hinge structure recognizes that the foot does not pivot on the ankle about a single pivot axis, but with a compound pivoting and sliding movement. Likewise, recognizing that the back does not pivot on the hips about a single axis, the hinge of the present invention finds utility in the construction of chairs, hinged beds, and the like. In a chair, for example, the back may be hinged to the seat with the sliding pivot axis hinge, thereby making the chair more comfortable to sit or rock in, as the chair back will both pivot and slide with respect to the seat.

While a certain illustrative embodiment of the present invention has been shown in the drawings and described in detail in the specification, it should be understood that there is no intention to limit the invention to the specific form and embodiments disclosed. On the contrary, the intention is to cover all modifications, alternative constructions, equivalents and uses falling within the spirit and scope of the invention as expressed in the appended claims.

We claim:

1. A floating pivot axis hinge comprising, in combination, a pair of juxtaposed hinge plates adapted to pivot and slide with respect to each other, each said plate having a pivot face in opposition to a pivot face on the juxtaposed plate, a concave groove in each of said faces, said concave grooves being substantially of equal length, a single pivot bearing ball positioned between said opposed faces and retained in said concave grooves, and means resiliently biasing said hinge plates together against said pivot bearing ball when said ball is positioned in said opposed grooves between said opposing faces, said pivot bearing ball thereby providing a floating pivot axis for hinge rotation of said hinge plates relative to each other, said concave grooves allowing said hinge plates to slide relative to each other and simultaneously pivot relative to each other about said floating pivot axis defined by said ball.

2. A floating pivot axis hinge as defined in claim 1 wherein said concave groove is tapered from a deeper point to a shallower point.

3. A floating pivot axis hinge as defined in claim 1 wherein said concave groove includes an inclined plane bottom surface.

4. A floating pivot axis hinge as defined in claim 1 wherein said concave groove is generally oval shaped having its widest point at its center and narrowest points at its ends.

5. A floating pivot axis hinge as defined in claim 4 wherein said groove is deepest at its widest point and shallowest at its narrowest point.

6. A floating pivot axis hinge for connecting first and second members for pivotal and partial sliding movement with respect to each other, said hinge comprising, in combination, a pair of juxtaposed hinge plates adapted to pivot and slide with respect to each other, each said plate having a pivot face in opposition to a pivot face on the juxtaposed plate, a concave groove in each of said faces, said concave grooves being substantially of equal length, each said groove having a deeper point and a shallower point, a single pivot bearing ball positioned between said opposed faces and retained in said concave grooves, and means resiliently biasing said hinge plates together against said pivot bearing ball when said ball is positioned in said opposed grooves between said opposing faces, said pivot bearing ball being located at the deeper point of each said groove when said members are aligned in parallel co-extensive relationship, said pivot bearing ball providing a floating pivot axis for hinge rotation of said hinge plates and thereby said members relative to each other, said concave grooves allowing said hinge plates to slide relative to each other and simultaneously pivot relative to each other about said floating pivot axis provided by said ball.

7. A hinge as defined in claim 6 wherein said first member is secured to one of said hinge plates and said second member is secured to the other of same hinge plates and including means on said one of said hinge plates for engaging said second member for limiting pivotally swinging movement of said members relative to each other about said floating pivot axis.

8. A hinge as defined in claim 7 wherein said limiting means comprises a cylindrical housing secured to one of said hinge plates and having a peripheral wall, means defining a circumferential slot in the peripheral wall of said housing for receiving said second member for limiting relative swinging movement thereof with respect to said housing.

9. A floating pivot axis hinge for an anatomical joint brace including a pair of brace arms adapted to be hinged together by said hinge, said hinge comprising, in combination, a pair of juxtaposed hinge plates adapted to pivot and slide with respect to each other, one of said plates being secured to one brace arm and the other being secured to the other brace arm, each said plate having a pivot face in opposition to a pivot face on the juxtaposed plate, a concave groove in each of said faces, said concave grooves being sustantially of equal length, each said groove having a deeper point and a shallower point, a single pivot bearing ball positioned between said opposed faces and retained in said concave grooves, and means resiliently biasing said hinge plates together against said pivot bearing ball when said ball is positioned in opposed grooves between said opposing faces, whereby said pivot bearing ball provides a floating pivot axis for hinge rotation and sliding movement of said hinge plates and thereby said brace arms relative to each other.

10. A hinge as defined in claim 9 wherein said biasing means comprises a spring.

11. A hinge as defined in claim 9 further including means for limiting pivotally swinging movement of said brace arms relative to each other about said floating pivot axis.

12. A hinge as defined in claim 11 wherein said limiting means comprises a cylindrical housing defined on one of said brace arms and having a peripheral wall, means defining a circumferential slot in the peripheral wall of said housing for receiving the other brace arm and means formed by said slot defining means for limiting swinging movement of the other brace arm with respect to said one brace arm.

13. A knee brace for a wearer's leg, said brace comprising a thigh cuff including inner and outer spaced brace arms adapted to extend respectively along the inside and outside of the thigh toward the knee, a calf cuff including inner and outer spaced calf brace arms adapted to extend respectively along the inside and outside of the calf and toward the knee, and floating pivot axis hinges rotatably connecting the respective inner and outer brace arms of each pair, each said hinge comprising, in combination, a pair of juxtaposed hinge plates adapted to pivot and slide with respect to each other, one of said plates being secured to a thigh brace arm and the other being secured to the corresponding calf brace arm, each said plate having a pivot face in opposition to a pivot face on the juxtaposed plate, a concave groove in each of said faces, said concave grooves being substantially of equal length, each said groove having a deeper point and a shallower point, a single pivot bearing ball positioned between said opposed faces and retained in said concave grooves, and means resiliently biasing said hinge plates together against said pivot bearing ball when said ball is positioned in said opposed grooves between said opposing faces, said pivot bearing ball being located at the deeper point of each said groove when said braces are aligned at an included angle corresponding to substantial extension of the wearer's leg, whereby said pivot bearing ball provides a floating pivot axis for hinge rotation of said hinge plates and thereby said brace arms relative to each other, said concave grooves allowing said hinge plates to slide relative to each other and simultaneously pivot relative to each other about said floating pivot axis provided by said ball during flexion and extension of the wearer's leg and knee.

14. A knee brace as defined in claim 13 wherein said biasing means comprises a spring.

15. A knee brace as defined in claim 13 further including means for limiting pivotally swinging movement of said thigh and calf braces relative to each other about said floating pivot axis.

16. A knee brace as defined in claim 15 wherein said limiting means comprises a cylindrical housing defined on each said thigh brace arm hinge plate and having a peripheral wall, means defining a circumferential slot in the peripheral wall of said housing for receiving a calf brace arm and limiting swinging movement thereof relative to said thigh brace arm.

* * * * *